(12) United States Patent
Chen

(10) Patent No.: US 8,105,276 B2
(45) Date of Patent: Jan. 31, 2012

(54) DISPOSABLE SAFETY INJECTION APPARATUS

(76) Inventor: Chang-Tzu Chen, Taipei (TW)

( * ) Notice: Subject to any disclaimer, the term of this patent is extended or adjusted under 35 U.S.C. 154(b) by 539 days.

(21) Appl. No.: 11/590,908

(22) Filed: Nov. 1, 2006

(65) Prior Publication Data

US 2007/0149923 A1    Jun. 28, 2007

(30) Foreign Application Priority Data

Jun. 22, 2006  (TW) ............................... 95210921 U

(51) Int. Cl.
*A61M 5/00*    (2006.01)
(52) U.S. Cl. ......................................... 604/110
(58) Field of Classification Search .................... 604/28, 604/110, 111, 193, 242–245, 218, 195, 198
See application file for complete search history.

(56) References Cited

U.S. PATENT DOCUMENTS 5,575,774 A * 11/1996 Chen .............................. 604/110
6,592,555 B1 * 7/2003 Wen-Pi et al. ................. 604/181

* cited by examiner

*Primary Examiner* — Theodore Stigell
(74) *Attorney, Agent, or Firm* — Guice Patents PLLC

(57) ABSTRACT

A disposable safety injection apparatus includes a liquid medication tube, a syringe needle, a push rod, and a tube ring. The syringe needle is connected to an insert tenon at a front end of the liquid medication tube. The insert tenon includes a connecting portion having concentric C-shape lacerable slot and circular lacerable slot respectively disposed at a connecting position of a top wall at the front end of the liquid medication tube and the connecting position of the top wall and an external side of the tube ring. A rod column having a latch portion is extended axially from the front end of the body of the push rod, passed through and fixed to the tube ring, such that the rod column can be slidably contained in liquid medication tube. The push rod is pushed forward to press the tube ring against top wall and latch the latch portion to a connecting portion in the insert tenon. The push rod is pushed further to lacerate the C-shape lacerable slot and form a torque onto a position having no groove, and thus the circular lacerable slot breaks at a thinner position and lacerates along the periphery. By then, the push rod is pulled backward to separate the liquid medication tube after the force is applied onto the circular lacerable slot.

11 Claims, 13 Drawing Sheets

DISPOSABLE SAFETY INJECTION APPARATUS

BACKGROUND OF THE INVENTION

1. Field of the Invention

The present invention relates to an injection apparatus, and more particularly to a disposable safety injection apparatus.

2. Description of the Related Art

As an injection apparatus such as a syringe has a substantial weight in the medical appliances. Particularly, some of the difficult-to-cure diseases including AIDS and various different types of hepatitis are spread in recent years, and thus infections caused by injections occur frequently and bring the attention of using medical appliances to people in different fields. As to syringes, using a safety disposable syringe with an autodisable function is a necessary and inevitable trend.

Basically, a traditional safety syringe includes a syringe needle, a liquid medication tube and a push rod. For example, a two-piece retractable safety syringe disclosed in R.O.C. Pat. No. 540385 issued on Jul. 1, 2003 includes a needle base disposed at a tube (or a liquid medication tube) for receiving the push rod, a lacerable slot disposed between the periphery of the needle base and the tube, a middle base disposed on the needle base and having a through hole, a latch member, and a push rod disposed at an end of the middle base and latched into the through hole, so as to constitute a safety syringe. After an end of the push rod is fixed to the needle base, the push rod retracts from the needle base and destroys the lacerable slot, such that the needle base fixed with a fixed syringe needle can be moved into the tube to prevent accidents or injuries caused by the exposed syringe needle.

The drawback of the aforementioned patent resides on that if the thickness of the lacerable slot is too large, say 0.12 mm, then the melted plastic liquid will flow into the gap to form a middle base with a through hole in the injection molding process. Since the groove is too thick and cannot be destroyed easily by external forces, and thus losing the autodisable function. If the thickness of the lacerable slot is too thin, say 0.06 mm, the lacerable slot can be destroyed easily by external forces, but the melted plastic liquid will not be able to pass through such a narrow slot, and the middle base with a through hole may not be formed integrally. Further, the lacerable slot at the top of the liquid medication tube comes with a weak design, and thus the needle base may be shaken by a torque produced by external forces during the injection or transportation process, or a leak may occur due to the crack of the lacerable slot.

SUMMARY OF THE INVENTION

In view of the shortcomings of the prior art, the inventor of the present invention based on years of experience on the design and marketing of the safety injection apparatus to conduct extensive experiments and tests in hope of overcoming the shortcomings of the traditional safety syringe, and finally developed a disposable safety injection apparatus in accordance with the present invention.

Therefore, it is a primary objective of the present invention to provide a disposable safety injection apparatus comprising: a liquid medication tube, a syringe needle, a push rod, and a tube ring, wherein the syringe needle is connected to an insert tenon at a front end of the liquid medication tube, and the insert tenon contains a connecting portion, and concentric C-shape lacerable slot and circular lacerable slot are disposed at connecting positions of a top wall at a front end of the liquid medication tube and connecting position of the top wall and an external side of the tube ring respectively. A rod column having a latch portion is extended axially from the body of the push rod and passed through and fixed to the tube ring, and thus the rod column can be slidably contained in liquid medication tube. When the push rod is pushed forward to press the tube ring against the top wall, and the latch portion is latched to a connecting portion of the insert tenon, and then the push rod is pushed further to tear the C-shape lacerable slot by a force, and produce a torque at a position having no groove to break a thinner position of a circular lacerable slot and a large break is spread along the periphery. By then, the push rod is pulled back to separate the liquid medication tube after a force is applied to the circular lacerable slot.

A secondary objective of the present invention is to provide a disposable safety injection apparatus that further comprises a positioning ring sheathed between the insert tenon and the tube ring and contacted with a top wall of the liquid medication tube. Alternatively, a base ring is protruded from a rear section of a needle base of the syringe needle and sheathed between the insert tenon and the tube ring, and an oblique end is disposed at a rear end and contacted with the top wall of the liquid medication tube.

A further objective of the present invention is to provide a disposable safety injection apparatus, wherein the connecting portion is a latch ring, and the latch portion is an arrow-shape latch tenon obliquely extended outward, and the latch tenon is latched to the latch ring.

Another further objective of the present invention is to provide a disposable safety injection apparatus, wherein the liquid medication tube has a stopping portion disposed at an opening at a rear end of the liquid medication tube, which is a connecting ring protruded inward, and a rod head portion of the push rod is comprised of a front-wing plate and a rear-wing plate, and the two wing plates can be latched and fixed at the connecting ring.

Another objective of the present invention is to provide a disposable safety injection apparatus, wherein the rod column has a radially protruded sliding portion comprised of the front and rear circular plates having an oblique surface separately on two peripheries and surrounding a circular hole at a rear side of the tube ring. If the tube ring presses against a top wall of the liquid medication tube, the two circular plates are entered into the circular chamber and slid therein, so that the rod column can continue moving forward.

Another object of the present invention is to provide a disposable safety injection apparatus, wherein the push rod has a rod head portion and a first breaking portion disposed sequentially at a front section of a rod body at a rear side of the rod column, and the rod head portion is latched to a stopping portion at an opening at a rear end of the liquid medication tube, so that the syringe needle, the front section of the push rod and the tube ring are contained in the liquid medication tube, and the push rod can break immediately at a first breaking portion. Further, the first breaking portion has a plug portion and a second breaking portion disposed sequentially at a rear side of the first breaking portion, and the plug portion is plugged into an opening at a front end of the liquid medication tube and the push rod breaks at a second breaking portion.

A further objective of the present invention is to provide a disposable safety injection apparatus, wherein a propping point is protruded on an internal side of a top wall of the connecting portion and the C-shape lacerable slot, such that when the push rod is pushed forward to latch the latch portion to the connecting portion in the insert tenon, and the rod column presses against the propping point, such that the C-shape lacerable slot is torn and broken by forces, and meanwhile, a torque is produced at a position having no groove to break at a thinner position of a circular lacerable slot breaks. The propping point is disposed at the middle between the connecting portion and the C-shape lacerable slot, and the propping point is a protruding point or a protruding rib.

BRIEF DESCRIPTION OF THE DRAWINGS

The objectives, shape, structure, apparatus, characteristics and effects will become apparent by the detail description together with the accompanying drawings as follows.

DETAILED DESCRIPTION OF THE PREFERRED EMBODIMENTS

Referring to FIGS. 1 to 4, for a disposable injection apparatus, the disposable injection apparatus comprises a liquid medication tube 1, a syringe needle 2, a push rod 3 and a tube ring 4.

Figure 3A:
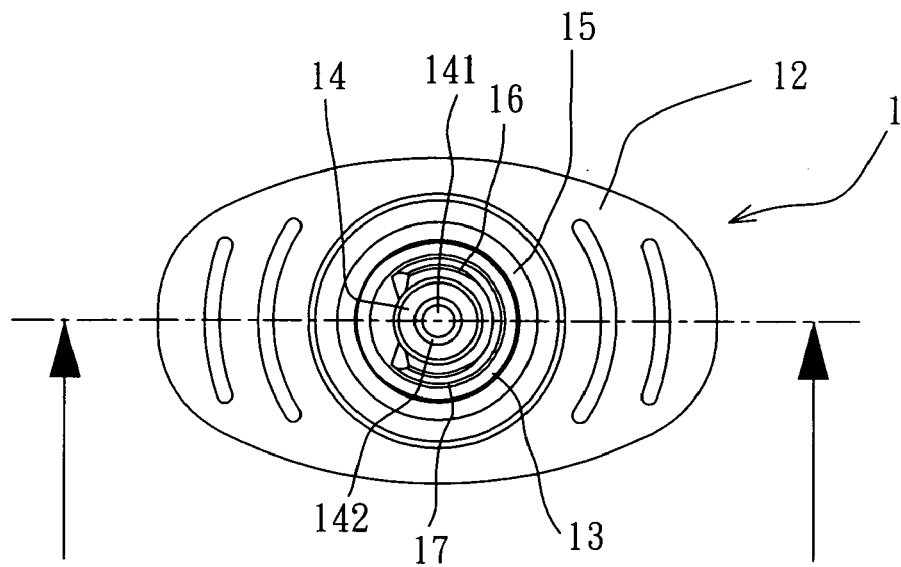
FIGS. 3a and 3b are a top view and a cross-sectional front view of a liquid medication tube of the present invention.
Figure 3B:
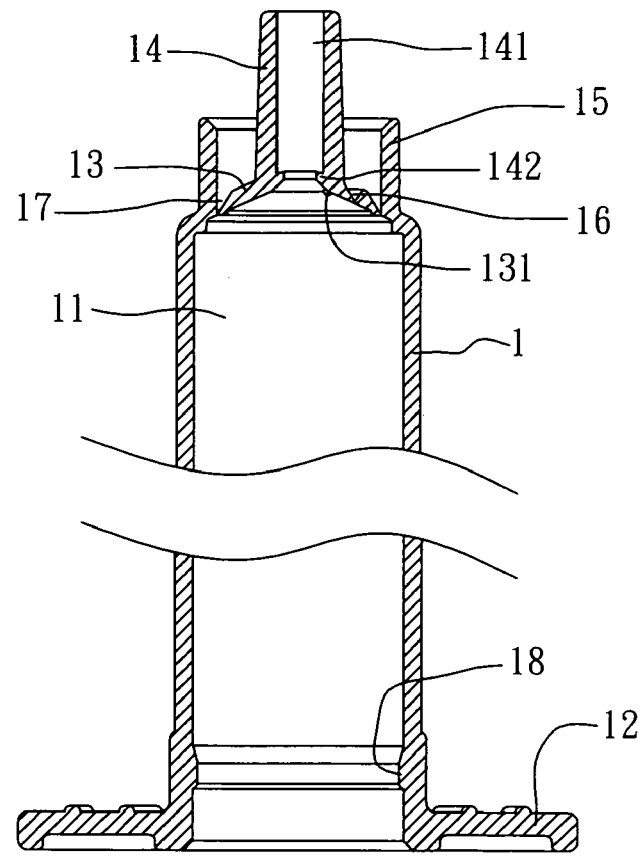

The liquid medication tube 1 is hollow and has a tube chamber 11 for containing a liquid medication, and its rear side has a pair of wing plates 12, so that users can hold the liquid medication tube 1 by the wing plates 12. The liquid medication tube 1 disposed at its top wall 13 at the front has an insert tenon 14 with a smaller external diameter and having a penetrating hole at its center as shown in FIGS. 3A and 3B. A C-shape lacerable slot 16 and a circular lacerable slot 17 are disposed respectively between the insert tenon 14 and the top wall 13 as well as the top wall 13 and the external side of the tube ring 15, and they come with a variable thickness such as 0.12 mm and 0.6 mm. The internal wall of the insert tenon 14 has an inwardly protruded connecting portion 142, and the internal side of the top wall 13 of the C-shape lacerable slot 16 has a propping point 131 protruded from the central position of the C-shape lacerable slot 16, wherein the propping point 131 is built for concentrating the exertion of forces. Therefore, the protruding point or protruding rib facilitates tearing and breaking the C-shape lacerable slot 16 in practical applications.

Further, the tube chamber 11 has a stopping portion 18 such as a connecting ring protruded from a position proximate to an opening at a rear end and latched to front and rear rod wings 331, 332 with an oblique surface of two peripheries of a rod head portion 33 of the push rod 3 to facilitate fixing the push rod 3 and breaking a rod neck 37.

Further, a positioning ring 5 is sheathed between the insert tenon 14 and the tube ring 15, and the positioning ring 5 can be made of a hard material or a soft material, but a soft elastic material such as rubber is preferred. In addition, the positioning ring 5 is contacted with the top wall 13 for preventing the insert tenon 14 from shaking due to the design of the two weak lacerable grooves 16, 17. If the two lacerable grooves 16, 17 are broken accidentally, then the positioning ring 5 further provides a function of preventing a leak.

Therefore, the purposes of installing the positioning ring 5 are given as follows: (1) Preventing the insert tenon 14 from causing an accidental crack or break at the two lacerable grooves 16, 17 due to a torque produced by external forces; and (2) Preventing a leak after the two lacerable grooves 16, 17 are cracked or broken accidentally, so as to maintain the injection function even if there is a small leak.

The syringe needle 2 is a prior art with a syringe needle 21 coupled to a needle base 22, and the middle of the needle base 22 has a base hole 23 interconnected to a needle hole of the syringe needle 21, and the internal diameter of the base hole 23 corresponds to the external diameter of the insert tenon 14 for a tight connection.

The push rod 3 is a bar-shape rod having a pushing plate 31 with a larger external diameter disposed at an end of the push rod 3, and a rod body is comprised of a plurality of radiating plates, and its front end has a rod head portion 33 and a rod column 34 extended axially from the front, and the rod column 34 has a sliding portion 35 protruded radially. The utmost front end of the rod column 34 is a latch portion 36, such as an arrow-shape latch tenon protruded obliquely outward.

The rod head portion 33 is comprised of front-wing and rear-wing plates 331, 332 having an oblique surface on each of two peripheries to facilitate latching the push rod 3 to the stopping portion 18, and facilitate breaking a first breaking portion 37 such as a rod neck tapered at an external diameter at the rear side of the rod head portion 33. The sliding portion 35 is comprised of front and rear circular plates 351, 352 having an oblique surface on the two peripheries for surrounding a circular hole 42 at a rear wall of the tube ring 4.

The present invention has a plug portion 38 and a tapered second breaking portion 39 such as a plug disposed sequentially at a rear side of the first breaking portion 37.

The tube ring 4 is made of a soft material, but not limited to rubber, and the external diameter and size of the tube ring 4 are corresponsive to the tube chamber 11 for a tight connection, and the rear side of the internal circular chamber 41 has a circular hole 42 for receiving the two circular plates 351, 352, and the front end has a smaller axial hole 43 for passing through the latch portion 36. The circular chamber 41 has a sufficient depth for sliding the two circular plates 351, 352 of the sliding portion 35 in the circular chamber 41.

Figure 1:
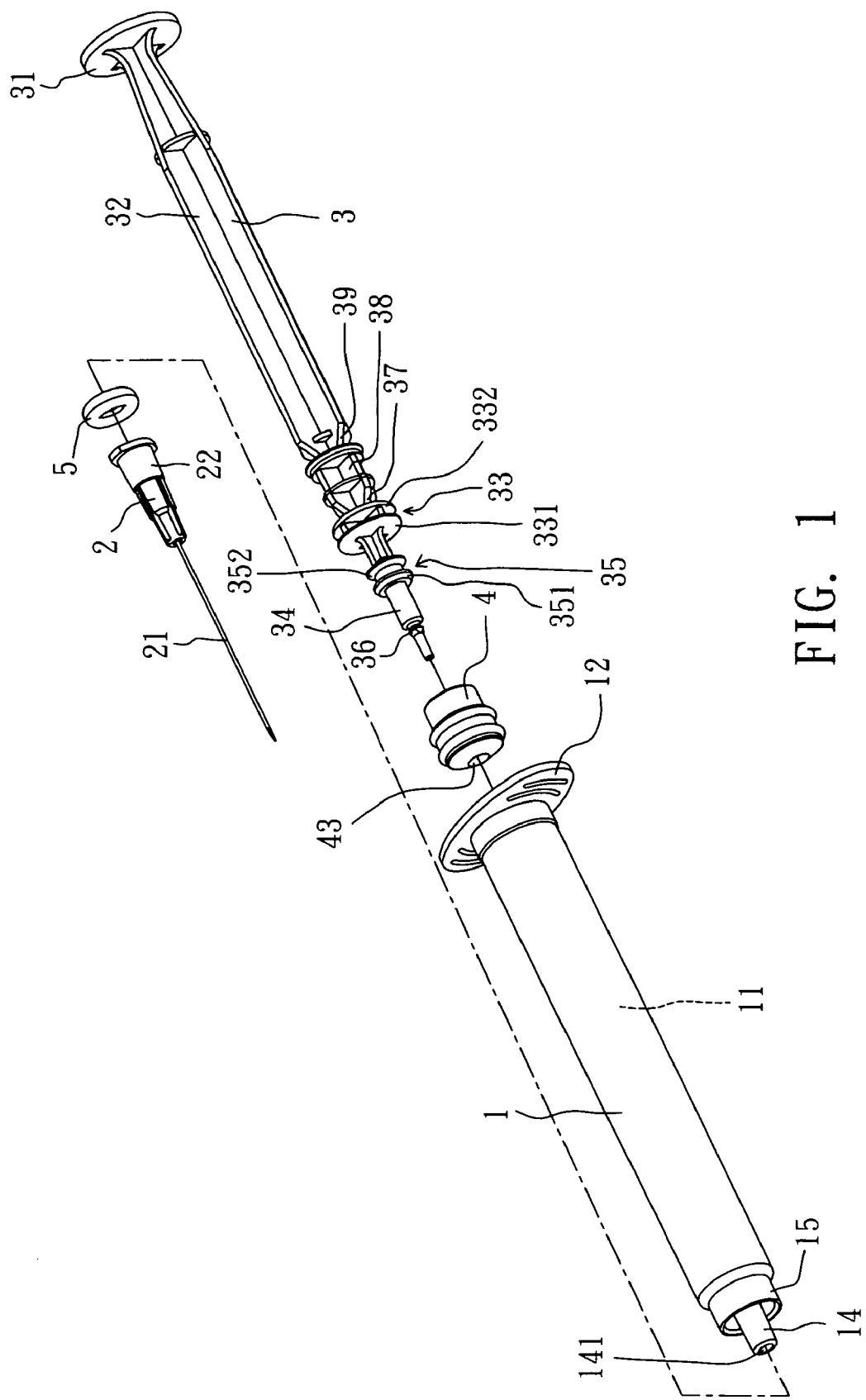
FIG. 1 is an exploded view of an injection apparatus in accordance with the present invention.
Figure 2:
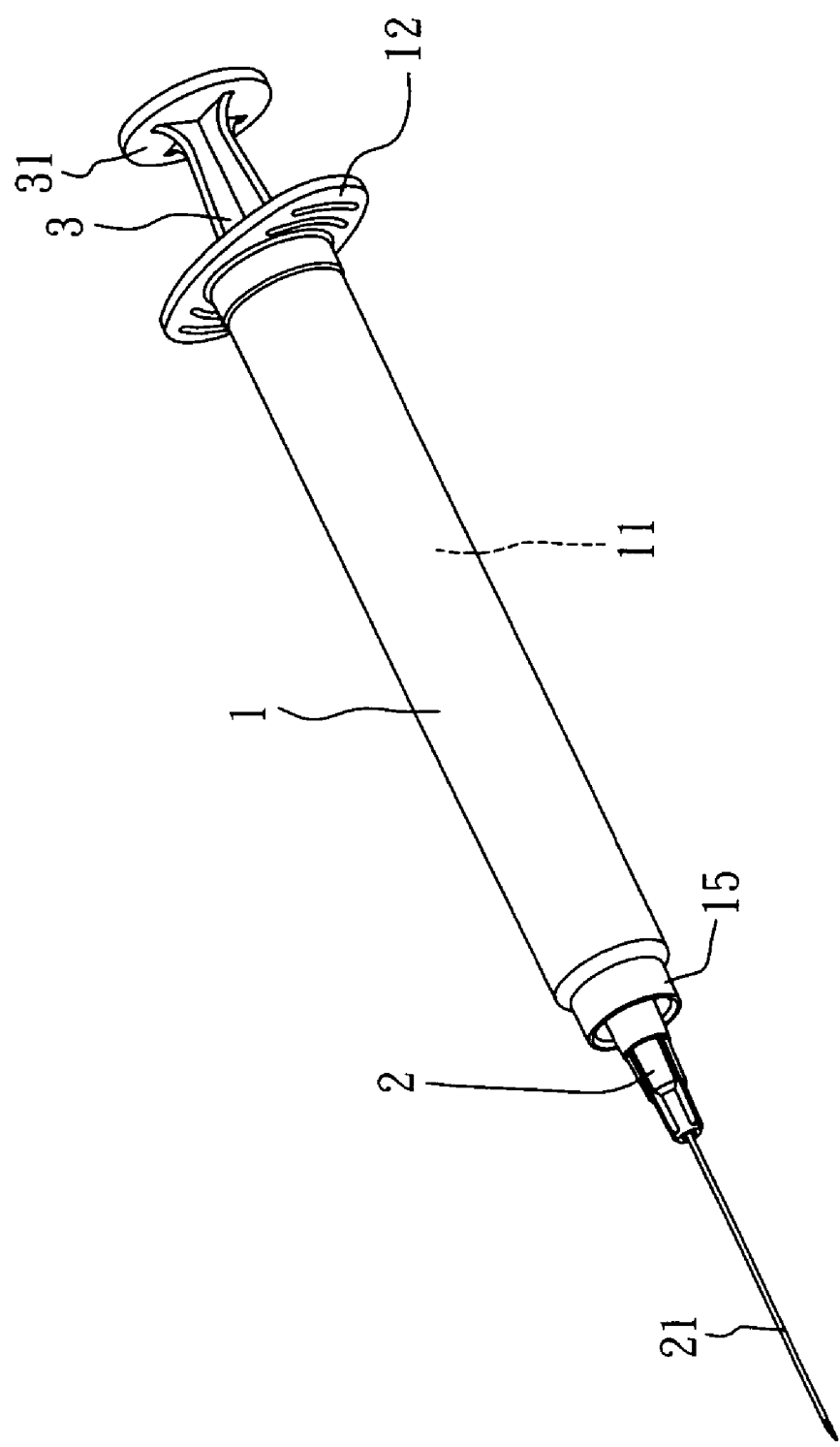
FIG. 2 is a perspective view of the present invention.
Figure 4:
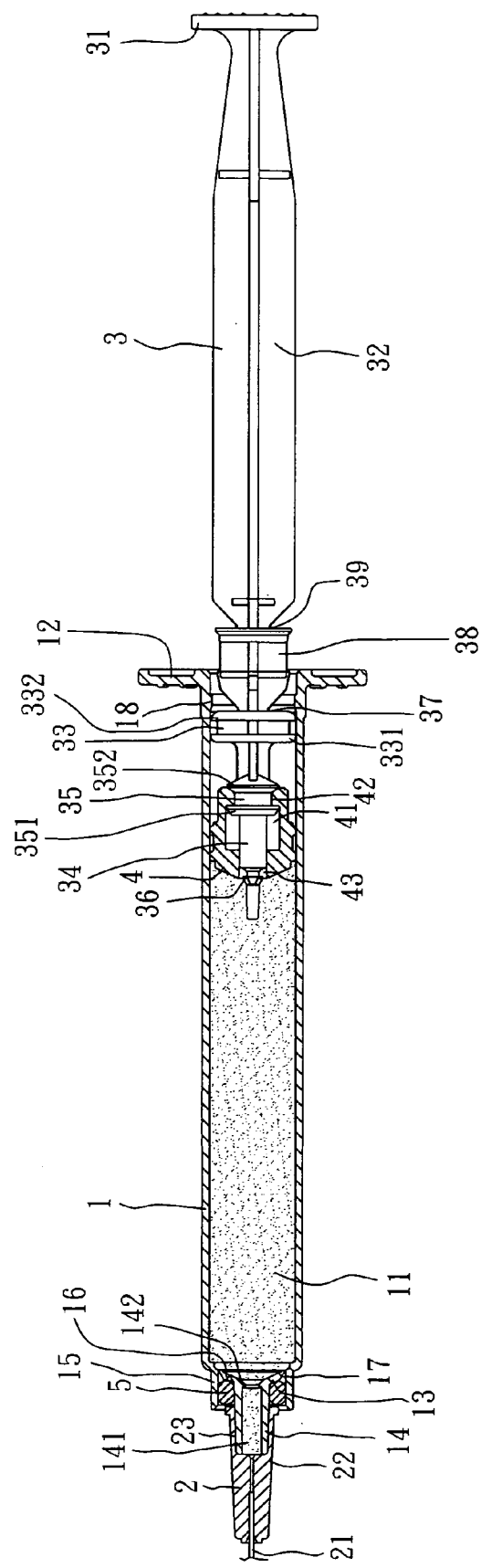
FIG. 4 is a cross-sectional view of drawing liquid medication into a liquid medication tube in accordance with the present invention.

In the figures, the tube ring 4 is engaged with the rod column 34 for assembling the disposable safety syringe of the invention, such that the latch portion 36 is passed out from the axial hole 43, and the two circular rings 351, 352 are engaged with the circular hole 42, and then the push rod 3 together with the tube ring 4 are embedded into the tube chamber 11 of the liquid medication tube 1, and the syringe needle 2 is connected to the insert tenon 14 through the needle base 22 as shown in the perspective view and the cross-sectional view of FIGS. 2 and 4 for drawing a liquid medication.

Figure 5:
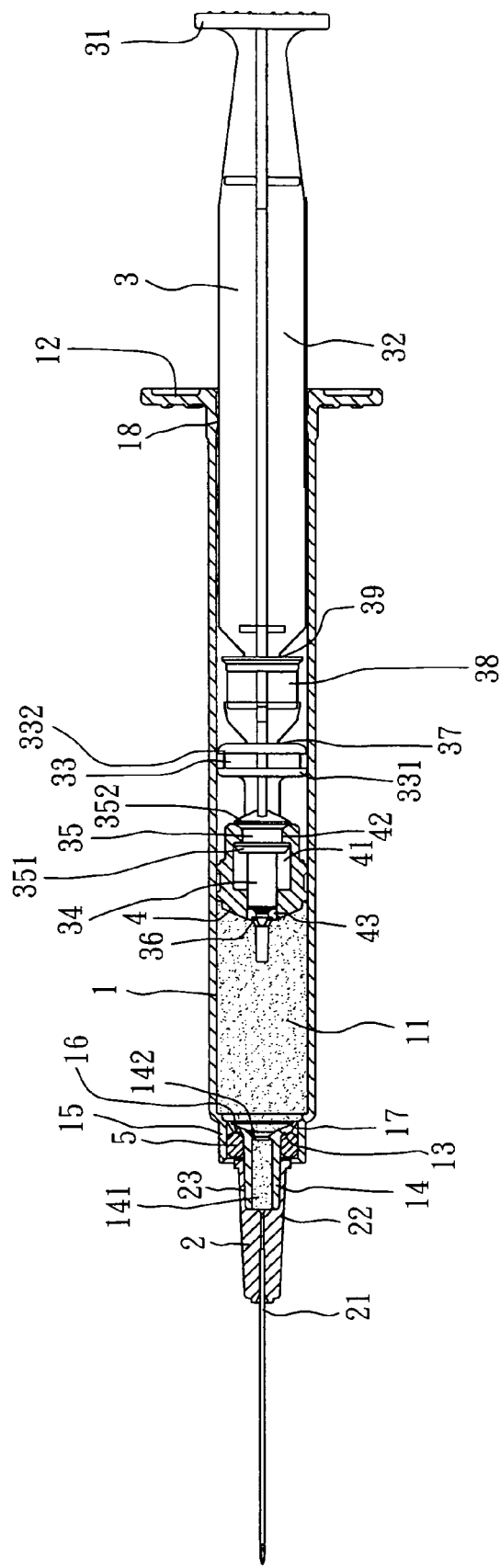
FIG. 5 is a cross-sectional view of performing an injection in accordance with the present invention.

Referring to FIG. 5, the liquid medication is drawn, and then applied or injected to the body of a user by pushing the push rod 3 by using a finger, so that the tube ring 4 at the front moves forward along the tube chamber 11 to compress the liquid medication and pass the liquid medication to the insert tenon 14 and the syringe needle 2, and inject the liquid medication into a user's body.

Figure 6:
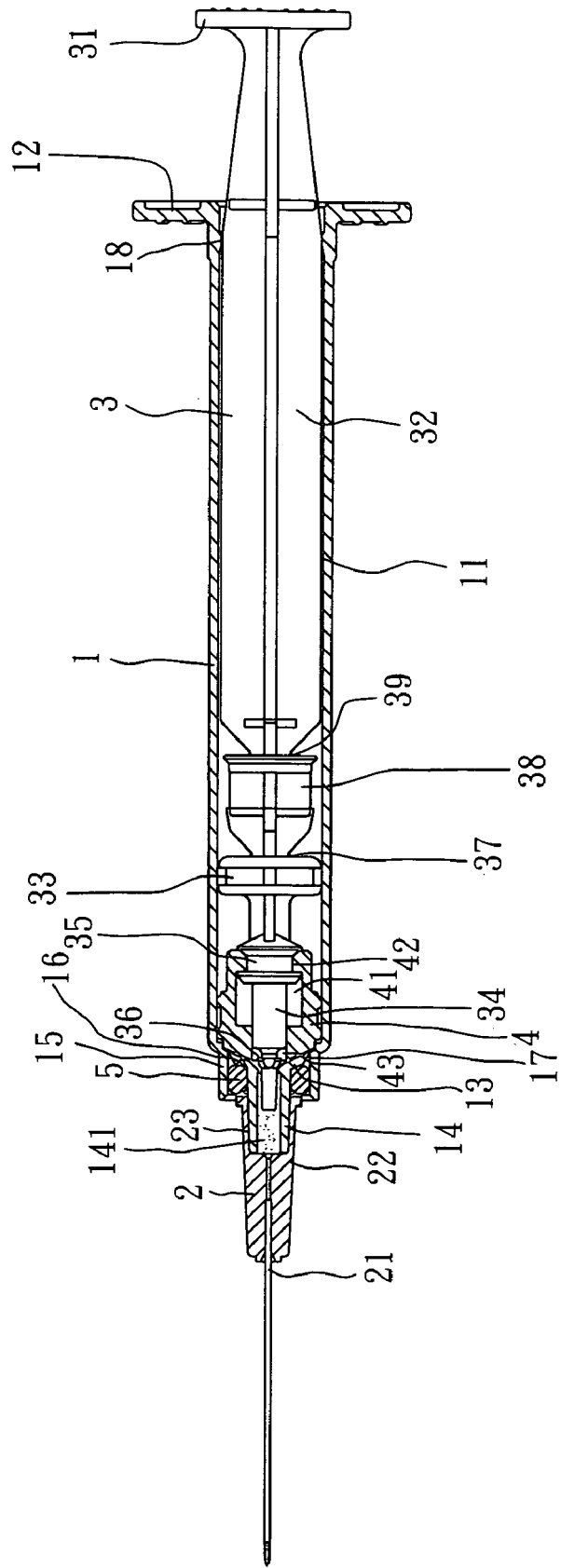
FIG. 6 is a cross-sectional view of performing an injection all the way to the end in accordance with the present invention.

Referring to FIG. 6, the liquid medication is squeezed out from the liquid medication tube 1 if the tube ring 4 together with the push rod 3 are pushed to the top wall 13 at the front end of the liquid medication tube 1, and the latch portion 36 is extended into the penetrating hole 13, so as to maximize the remaining liquid medication.

Figure 7:
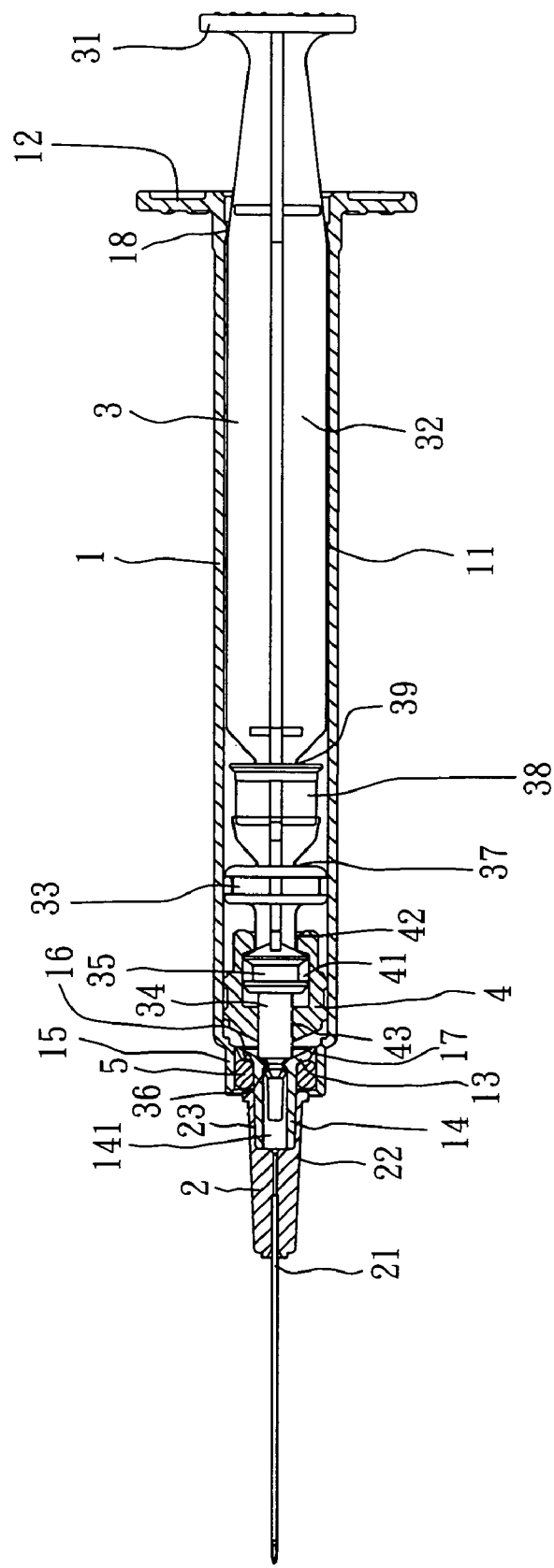
FIG. 7 is an enlarged cross-sectional view of latching a rod protrusion to a latch ring in accordance with the present invention.

Referring to FIG. 7, the push rod 3 is pushed forward after the injection is completed, such that the latch portion 36 is latched to the connecting portion 142 in the insert tenon 14, and the two front and rear circular wings 351, 352 of the sliding portion 35 press the tube ring 4 against the top wall 13. The push rod 3 continues moving forward and enters into the circular chamber 41.

Figure 8A:
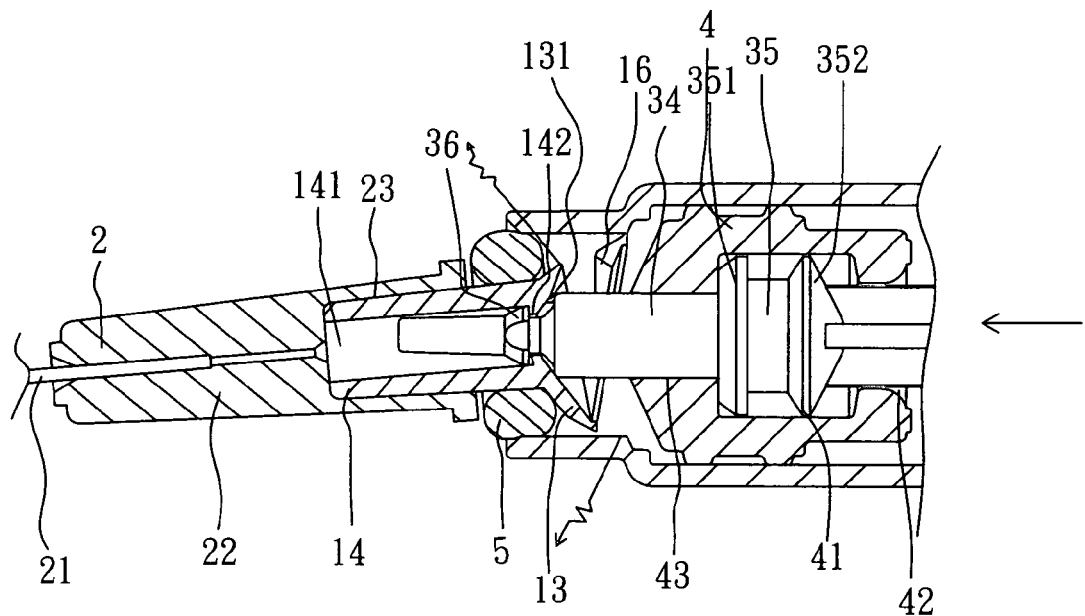
FIGS. 8a and 8b are enlarged cross-sectional views of a process of tearing a lacerable groove of a liquid medication tube in accordance with the present invention.

Referring to FIG. 8a, the rod column 34 presses against the propping point 131 if the push rod 3 continues moving forward, such that the C-shape lacerable slot 16 will be torn and broken by the forces. In the meantime, a torque is produced at a position having no groove, so as to break a circular lacerable slot 17 at a thinner position and spread the break along the periphery, but the slot is not cut off completely.

Figure 8B:
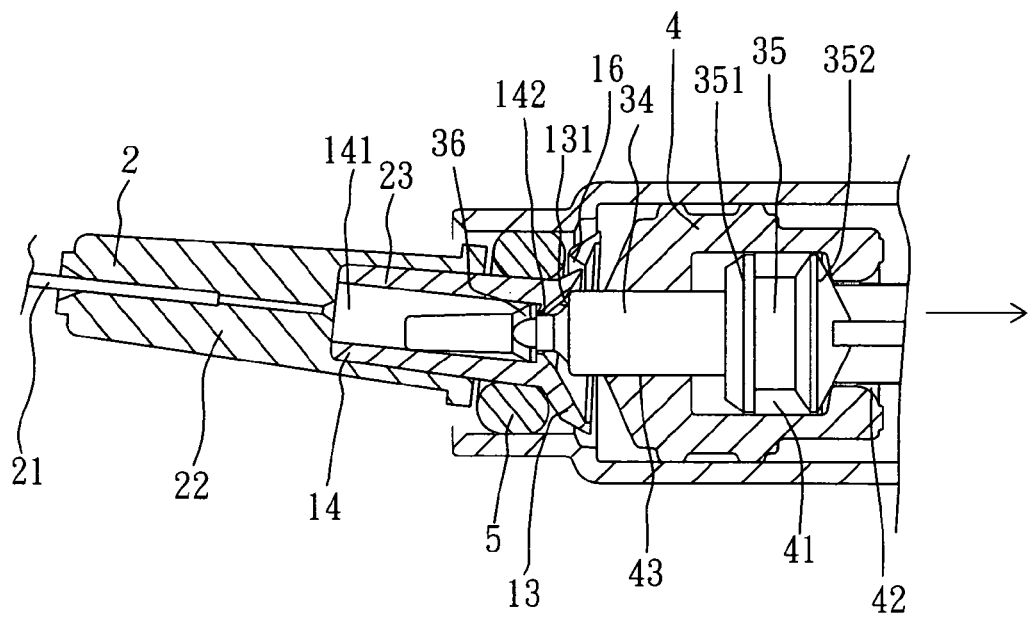
Figure 9:
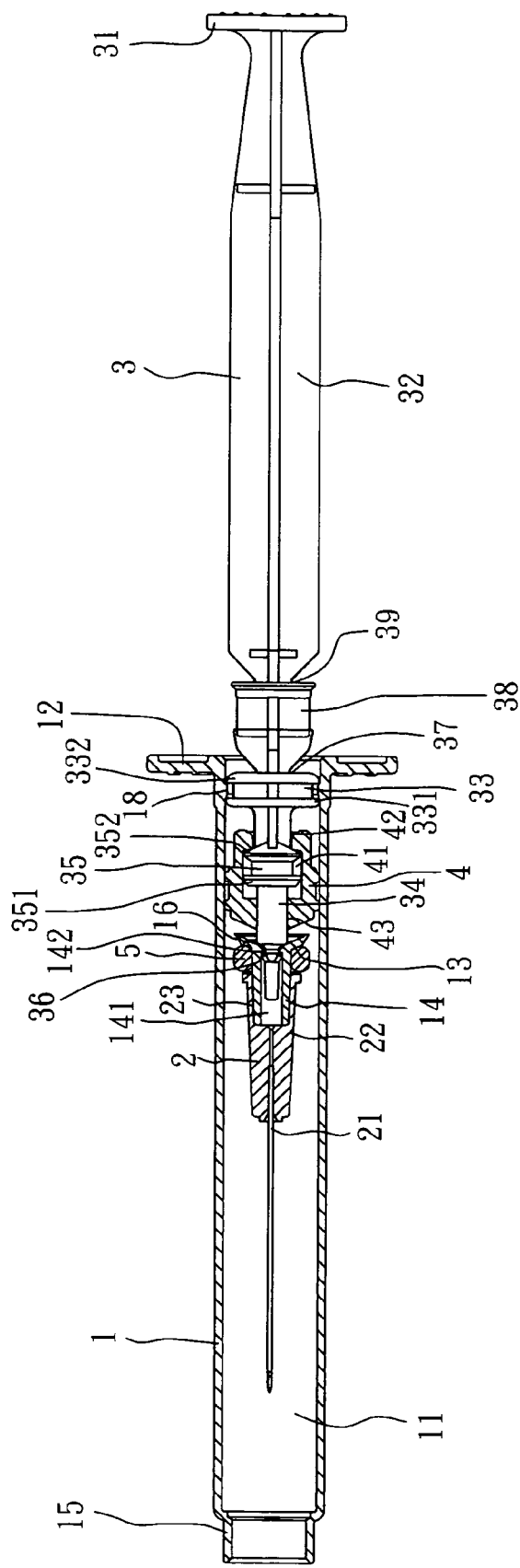
FIG. 9 is a schematic view of pulling back a push rod in accordance with the present invention.

Referring to FIG. 8b, the push rod 3 is retracted and separated completely from the liquid medication tube 1 after a force is applied onto the circular lacerable slot 17 as shown in FIG. 9, and the push rod 3 together with the tube ring 4, insert tenon 14, positioning ring 5 and syringe needle 2 are pulled back into the tube chamber 11, until the stopping portion 18 disposed at an opening at a rear end of the tube chamber 11 is latched to the rod head portion 35, such that the push rod 3 will not be pulled back to achieve the effect of preventing any reuse.

Figure 10:
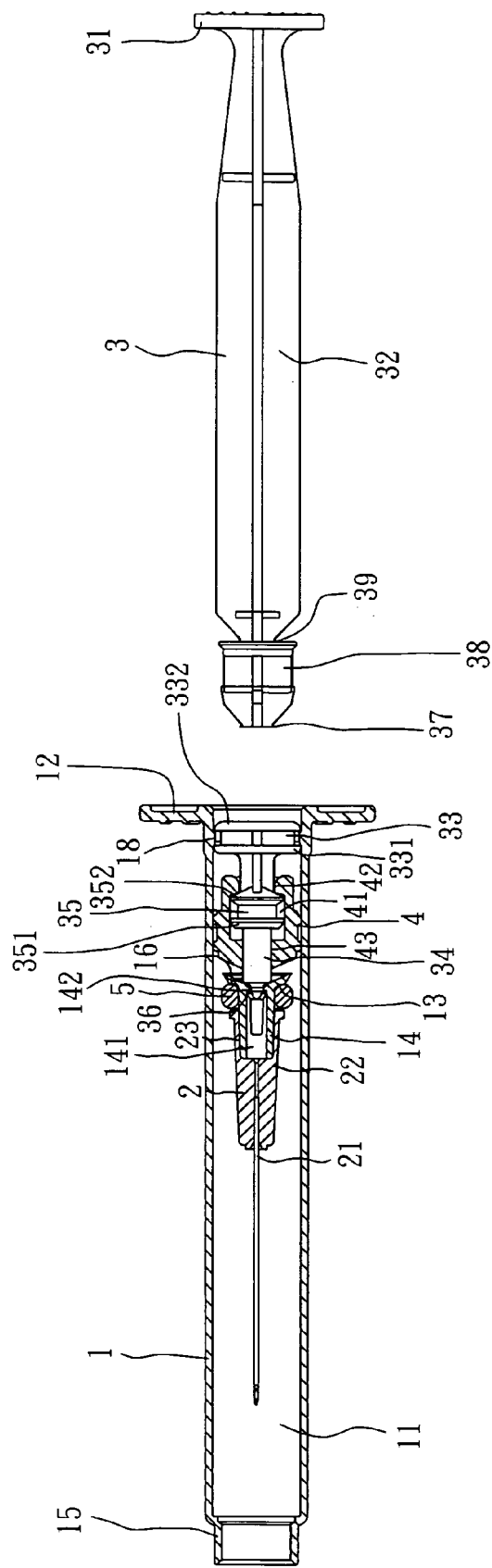
FIG. 10 is a schematic view of breaking a push rod at an opening at a rear end of a liquid medication tube in accordance with the present invention.

Referring to FIG. 10, the push rod 3 breaks at a first breaking portion 37, so that the syringe needle 2, a portion of the push rod 3, and the tube ring 4 remain in the tube chamber 11.

Figure 11:
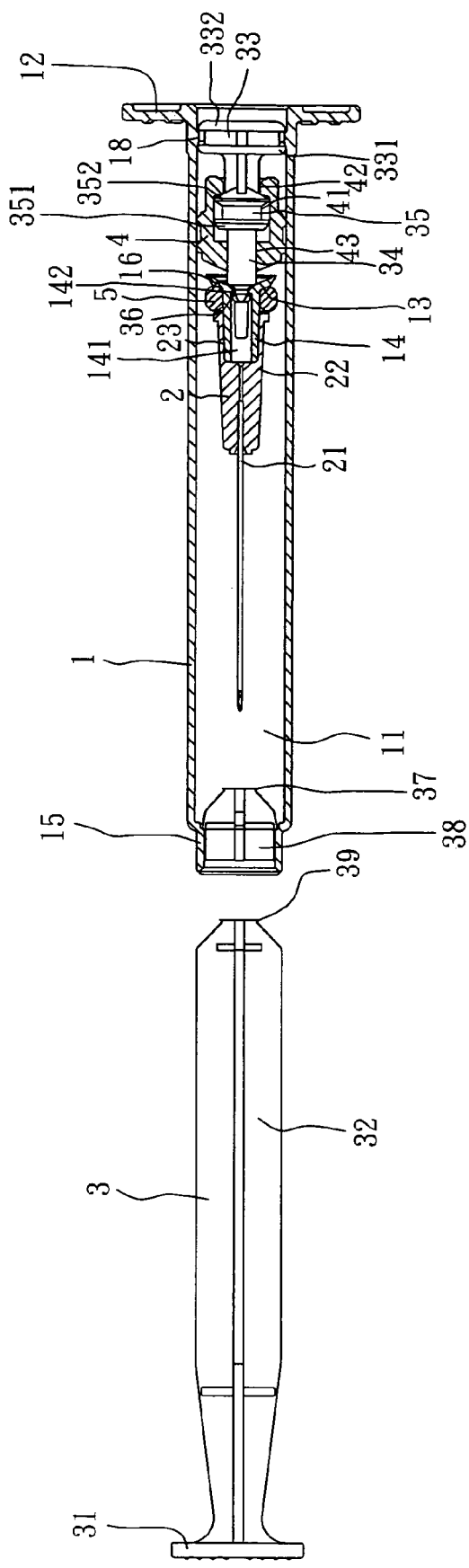
FIG. 11 is a schematic view of plugging a rod plug of a push rod into an opening at a front end of a liquid medication tube in accordance with the present invention.

Referring to FIG. 11, the plug portion 38 of a broken push rod 3 is plugged into an opening at a front end of the liquid medication tube 1, and the push rod 3 breaks at a second breaking portion 39, and the openings at both ends of the liquid medication tube 1 are sealed by the rod head portion 33 and the plug portion respectively. Then, the liquid medication tube 1 will be disposed without any safety concern.

Figure 12:
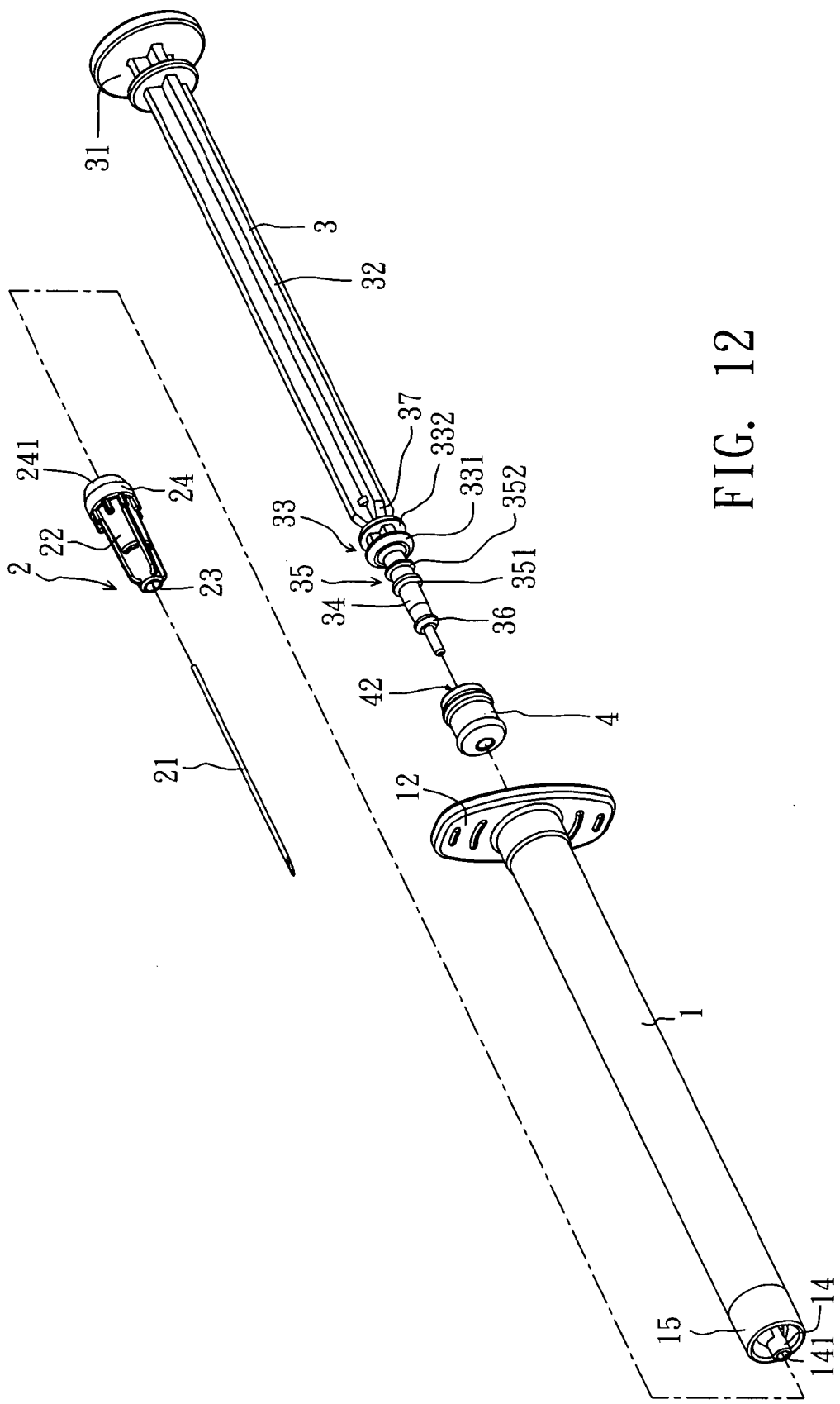
FIG. 12 is an exploded view of a safety injection apparatus in accordance with another preferred embodiment of the present invention.
Figure 13:
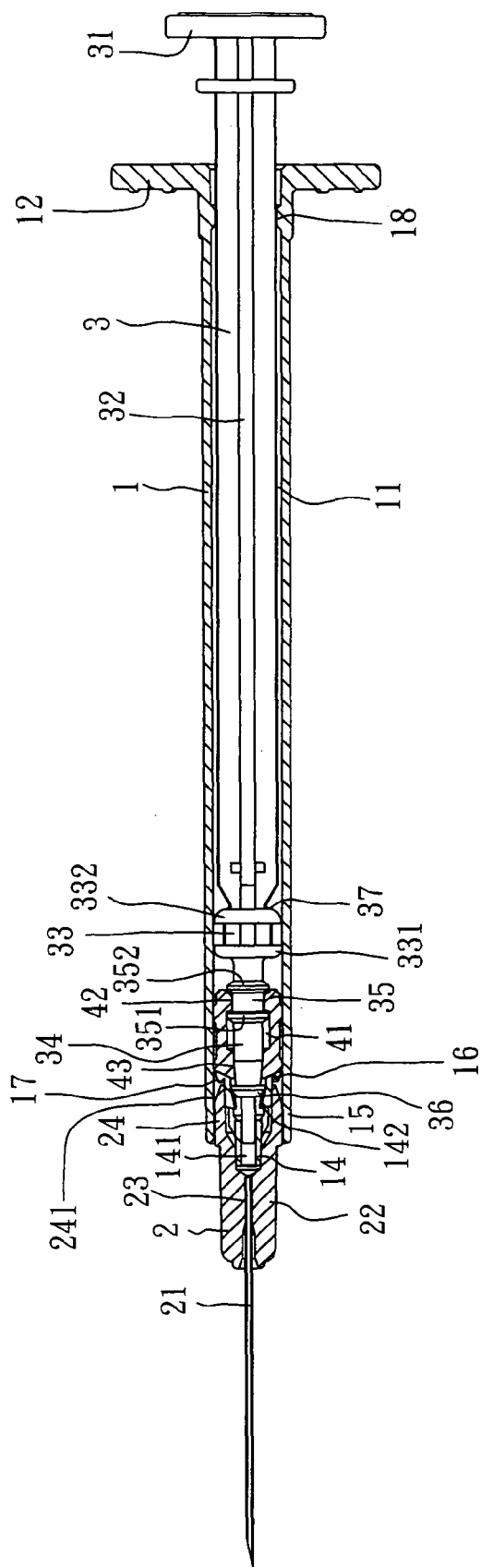
FIG. 13 is a cross-sectional view of an assembled safety injection apparatus as depicted in FIG. 12.

Referring to FIGS. 12 and 13 for another preferred embodiment of a disposable safety injection apparatus in accordance with the present invention, elements shown in FIGS. 12 and 13 and identical to those in the foregoing preferred embodiments are named and labeled with same numerals, and the only difference resides on that this embodiment does not have a positioning ring, but installs a base ring 24 at a rear section of a needle base 22 of the syringe needle 2 and sheathed between the insert tenon 14 and the tube ring 15, and the rear side has an oblique end 241.

The oblique end 241 is contacted with the top wall 16, and such arrangement can prevent any shaking of the insert tenon 14 due to the design of weak surfaces of the two lacerable grooves 16, 17. If the two lacerable grooves 16, 17 are cracked or broken accidentally, the oblique end 241 can achieve the effect of preventing a leak.

In the practice of the present invention, the syringe needle cannot be pushed forward after the injection is performed, so as to effectively prevent any reuse of the injection apparatus. In the design of the positioning ring or an oblique end of the base ring at the rear section of the syringe needle being sheathed between the insert tenon and the tube ring, the insert tenon can be prevented from shaking due to the weak surface of the lacerable grooves, and the design also has the effect of preventing a leak. After the medication is applied or injected, the openings at both ends of the liquid medication tube are sealed by the rod head portion and the plug portion, and the used syringe needle cannot be exposed from the liquid medication tube, and thus improving the safety of the use. Further, the design of the concentric C-shape lacerable slot and circular lacerable slot uses the pushing and pulling forces of the push rod to drive the top wall together with the insert tenon and syringe needle to be separately completely from the liquid medication tube to define an autodisable function. The present invention is definitely a novel improvement over the prior art.

While the invention has been described by means of a specific numerous modifications and variations could be made thereto by those skilled in the art without departing from the scope and spirit of he invention set forth in the claims.

In summation of the above description, the present invention definitely achieves the expected objective and provides an engraving method for a laser engraver to enhance the performance over the prior art. The invention further complies with the patent application requirements and is duly filed for the patent application.

What is claimed is:

1. A disposable safety injection apparatus comprising,
a liquid medication tube;
a syringe needle;
a push rod;
a tube ring;
said syringe needle is coupled to an insert tenon disposed at a front end of said liquid medication tube;
said insert tenon comprises a connecting portion disposed therein, a concentric C-shape lacerable slot, and a circular lacerable slot wherein,
the C-shape lacerable slot is disposed between the insert tenon and a top wall of the liquid medication tube; and
the circular lacerable slot is disposed between the top wall of the liquid medication tube and an external side of a liquid medication tube ring located on said front end of said liquid medication tube;
a body of said push rod includes a rod column having a latch portion being extended axially from a front end of said push rod and passed through and fixed to said tube ring;
said push rod is slidably contained in the liquid medication tube wherein,
said push rod is pushed forward to press said tube ring against said top wall, and said latch portion is latched to said connecting portion in said insert tenon;
said push rod is pushed to tear said C-shape lacerable slot and form a torque at a portion having no groove and break a thinner portion corresponding to a position of said circular lacerable slot;
said push rod comprises a rod head portion and a first breaking portion disposed sequentially at a front section of the body of the push rod;

said rod head portion is latched to a stopping portion at an opening at a rear end of said liquid medication tube, wherein said syringe needle, a front section of said push rod, and said tube ring are accommodated in said liquid medication tube, and said push rod is selectively broken at a first breaking portion thereof.

2. The disposable safety injection apparatus of claim 1, wherein said C-shape lacerable slot and the circular lacerable slot are of variable thickness.

3. The disposable safety injection apparatus of claim 1, further comprising a positioning ring sheathed between said insert tenon and said liquid medication tube ring and contacted with a top wall of said liquid medication tube.

4. The disposable safety injection apparatus of claim 1, wherein said connecting portion is a latch ring, and said latch portion is an arrow-shaped latch tenon extended obliquely outward and latched to said latch ring.

5. The disposable safety injection apparatus of claim 1, wherein said liquid medication tube has a stopping portion disposed at an opening at a rear end of said liquid medication tube, and is an inwardly protruded connecting ring, and a rod head portion of said push rod is comprised of a front-wing plate and a rear-wing plate, and said two wing plates are latched and fixed to said connecting ring.

6. The disposable safety injection apparatus of claim 1, wherein said rod column has a sliding portion protruded radially from said rod column and comprised of front and rear circular plates having an oblique surface separately at two peripheries for jointly clamping a circular hole at the rear of said tube ring, such that when said tube ring presses against said top wall of said liquid medication tube, said two circular plates are entered into a circular chamber and slid therein, and said rod column can continue moving forward.

7. The disposable safety injection apparatus of claim 1, wherein said syringe needle has a base ring protruded from a rear section of a needle base and sheathed between said insert tenon and said liquid medication tube ring, and an oblique end disposed at a rear side and contacted with said top wall of said liquid medication tube.

8. The disposable safety injection apparatus of claim 1, wherein said first breaking portion has a plug portion and a second breaking portion disposed sequentially at a rear side of said first breaking portion, and said plug portion is embedded at an opening at a front end of said liquid medication tube, and said push rod is broken at a second breaking portion.

9. The disposable safety injection apparatus of claim 1, wherein said top wall of said connecting portion and said C-shape lacerable slot has a propping point disposed on an internal surface of said top wall, such that when said push rod is pushed forward, said latch portion is latched to a connecting portion in said insert tenon, and said rod column presses against said propping point to gradually tear said C-shape lacerable slot while forming a torque at a position having no groove, so as to break a circular lacerable slot at a corresponding thinner portion.

10. The disposable safety injection apparatus of claim 9, wherein said propping point is disposed at the middle between said connecting portion and said C-shape lacerable slot.

11. The disposable safety injection apparatus of claim 9, wherein said propping point is a protruding point or a protruding rib for concentrating the exertion of a force.

* * * * *